US009408819B2

(12) United States Patent
Herz et al.

(10) Patent No.: US 9,408,819 B2
(45) Date of Patent: *Aug. 9, 2016

(54) METHOD FOR REDUCING OR PREVENTING SYSTEMIC INFLAMMATION (75) Inventors: Udo Herz, Evansville, IN (US); Robert J. McMahon, Evansville, IN (US); William Michael Russell, Evansville, IN (US); Josef Neu, Gainesville, FL (US)

(73) Assignee: Mead Johnson Nutrition Company, Glenview, IL (US)

( * ) Notice: Subject to any disclaimer, the term of this patent is extended or adjusted under 35 U.S.C. 154(b) by 2028 days.

This patent is subject to a terminal disclaimer.

(21) Appl. No.: 12/035,718

(22) Filed: Feb. 22, 2008

(65) Prior Publication Data
US 2008/0206213 A1    Aug. 28, 2008

Related U.S. Application Data (60) Provisional application No. 60/904,122, filed on Feb. 28, 2007.

(51) Int. Cl.
*A61K 31/202* (2006.01)
*A61K 35/745* (2015.01)
*A61K 35/747* (2015.01)

(52) U.S. Cl.
CPC ............. *A61K 31/202* (2013.01); *A61K 35/745* (2013.01); *A61K 35/747* (2013.01)

(58) Field of Classification Search
CPC .................. A23V 2002/00; A23V 2200/3204; A23V 2250/1868; A23V 2200/3202; A23V 2250/1578; A23V 2250/1862; A23V 2250/18; A23V 2250/54252; A23V 2250/28; A23V 2250/304; A23V 2250/5034; A23V 2250/0644; A23V 2250/2116; A23V 2200/324; A23V 2200/32; A23V 2250/211; A23V 2200/332; A61K 2300/00; A61K 35/747; A61K 35/745; A61K 35/744; A61K 31/202; A61K 35/741; A61K 31/4164; A61K 31/454; A61K 31/496; A61K 31/519; A61K 31/52; A61K 31/5375; A61K 31/606; A61K 31/635; A61K 38/13
See application file for complete search history.

(56) References Cited

U.S. PATENT DOCUMENTS

| | | | |
|---|---|---|---|
| 5,705,160 A | 1/1998 | Bruce et al. | |
| 5,804,179 A | 9/1998 | Bruce et al. | |
| 6,156,320 A * | 12/2000 | Izvekova et al. | 424/197.11 |
| 6,180,100 B1 | 1/2001 | Bruce et al. | |
| 6,331,140 B1 | 12/2001 | Mollet et al. | |
| 6,358,521 B1 * | 3/2002 | Izvekova et al. | 424/439 |
| 6,399,055 B1 | 6/2002 | Postaire et al. | |
| 6,479,051 B1 | 11/2002 | Bruce et al. | |
| 6,797,266 B2 | 9/2004 | Naidu | |
| 7,090,840 B2 | 8/2006 | Cho | |
| 7,125,963 B2 | 10/2006 | Naidu | |
| 2002/0006432 A1 | 1/2002 | Collins et al. | |
| 2003/0091549 A1 | 5/2003 | Collins et al. | |
| 2003/0092163 A1 | 5/2003 | Collins et al. | |
| 2003/0113306 A1 | 6/2003 | Collins et al. | |
| 2003/0166257 A1 | 9/2003 | Collins et al. | |
| 2003/0170217 A1 | 9/2003 | Collins et al. | |
| 2003/0215467 A1 | 11/2003 | Collins et al. | |
| 2004/0115178 A1 | 6/2004 | Schiffrin et al. | |
| 2004/0208863 A1 | 10/2004 | Versalovic et al. | |
| 2005/0074441 A1 | 4/2005 | Collins et al. | |
| 2005/0084482 A1 | 4/2005 | Collins et al. | |
| 2005/0100531 A1 | 5/2005 | Bienenstock | |
| 2005/0180962 A1 | 8/2005 | Raz et al. | |
| 2005/0214272 A1 | 9/2005 | Collins et al. | |
| 2005/0244392 A1 | 11/2005 | Pei et al. | |
| 2006/0002908 A1 | 1/2006 | Collins et al. | |
| 2006/0078547 A1 | 4/2006 | Collins et al. | |
| 2006/0088514 A1 | 4/2006 | O'Mahony et al. | |
| 2006/0233752 A1 | 10/2006 | McMahon et al. | |
| 2006/0233762 A1 | 10/2006 | McMahon et al. | |
| 2006/0292133 A1 | 12/2006 | Collins et al. | |
| 2007/0031393 A1 | 2/2007 | Trejo et al. | |

FOREIGN PATENT DOCUMENTS

| | | | |
|---|---|---|---|
| WO | WO 97/00078 | * | 1/1997 |
| WO | 20060124630 | * | 11/2006 |
| WO | WO 2006124630 A2 | * | 11/2006 |

OTHER PUBLICATIONS

Kaila et al., "Viable ver. inativ. lactobacillus strain GG in acute rotavirus diarrhoea", Archives of Disease in Childhood, 1995; 72: 51-53.*
International Search Report of the International Searching Authority for application No. PCT/US2008/054710, International filing date Feb. 22, 2008. Date of mailing Jun. 23, 2008.
Zhang, L., et al., *Alive and Dead Lactobacillus rhamnosus GG Decrease tumor necrosis Factor-α-induced Interleukin-8 Production in Caco-2 Cells*, Journal of Nutrition, Wistar Institute of Anatomy and Biology, vol. 135, No. 7, Jul. 1, 2005, pp. 1752-1758.
Kankaanpaa, P., et al., *Homogenates derived from probiotic bacteria provide down-regulatory signals for peripheral blood mononuclear cells*, Food Chemistry, Elsevier Science Publishers Ltd., vol. 83, No. 2, Nov. 1, 2003, pp. 269-277.
Zhang, L., et al., *Lactobacillus rhamnosus GG Decreases Lipopolysaccharide-induced Systemic Inflammation in a Gastrostomy-fed Infant Rat Model*, Jour. of Ped. Gastroenterology and Nutr., vol. 42, No. 5, May 1, 2006, pp. 545-552.
Jeschke, et al., *Insulin Attenuates the Systemic Inflammatory Response to Thermal Trauma*, Mol. Med. 8(8):443-450 (2002).
Murch, S.H., *Toll of Allergy Reduced by Probiotics*, Lancet, 357:1057-1059 (2001).

(Continued)

Primary Examiner — Debbie K Ware
(74) Attorney, Agent, or Firm — Patterson Intellectual Property Law, P.C.; James R. Cartiglia; Bethany J. Whelan (57) ABSTRACT The present disclosure is directed to a novel nutritional formula for treating or preventing systemic inflammation in a subject. The nutritional formula comprises a therapeutically effective amount of inactivated *Lactobacillus rhamnosus* GG (LGG).

20 Claims, 6 Drawing Sheets

(56) References Cited

OTHER PUBLICATIONS

Hooper, et al., *How Host-Microbial Interactions Shape the Nutrient Environment of the Mammalian Intestine*, Annu. Rev. Nutr. 22:283-307 (2002).

Bourlioux, et al., *The Intestine and its Microflora are Partners for the Protection of the host: Report on the Danone Symposium "The Intelligent Intestine,"* held in Paris, Jun. 14, 2002, Am. J. Clin. Nutr. 78:675 (2003).

Hooper, L.V., & Gordon, J.I., *Commensal Host-Bacterial Relationships in the Gut*, Sci. 292:1115 (2001).

Haller, et al., *Non-Pathogenic Bacteria Elicit a Differential cytokine Response by Intestinal Epithelial Cell/Leucocyte Co-Cultures*, GUT 47:79 (2000).

Walker, W.A., *Role of Nutrients and Bacterial colonization in the Development of Intestinal Host Defense*, J. Pediatr. Gastoenterol. Nutr. 30:S2 (2000).

Isolauri, E., et al., *Probiotics: Effects on Immunity*, Am. J. Clin. Nutr. 73:444S-50S (2001).

Agostoni, et al., *Probiotic Bacteria in Dietetic Products for Infants: A Commentary by the ESPGHAN Committee on Nutrition*, J. Pediatr. Gastro. Nutr. 38:365-374 (Apr. 2004).

Fuller, R., *Probiotics in Man and Animals*, J. Appl. Bacteriol. 66:365-78 (1989).

MacGregor, G., et al., *Yoghurt biotherapy: contraindicated in immunosuppressed patients?* Postgrad Med J. 78:366-367 (2002).

Kirjavainen, P., et al., *Probiotic Bacteria in the Management of Atopic Disease: Underscoring the Importance of Viability*, J. Ped. Gastro. 36:223-227 (2003).

Lawrence, et al., *Possible New Role for NFkB in the Resolution of Inflammation*, Nature Med. 7:1291 (2001).

Majamaa, Heli, et al., *Lactic Acid Bacteria in the Treatment of acute Rotavirus Gastroenteritis*, J. Ped. Gastro. and Nutr., 20:333-338 (1995).

Ouwehand, A.C., et al., *Adhesion of inactivated probiotic strains to intestinal mucus*, The Society for Applied Microbiology, Letters in Applied Microbiology, 31:82-86 (2000).

Isolauri, E, et al., *Probiotics: a role in the treatment of intestinal infection and inflammation?*, GUT, vol. 50, p. iii54-iii59 (2002).

Kaila, Minna, *Nutritional management of acute diarrhea—Lactobacillus GG*, Today (1996).

Heyman, Martine, *Effect of Lactic Acid Bacteria on Diarrheal Diseases*, J. of the Amer. College of Nutr., 19:137-146 (2000).

Anuradha, S, et al., *Probiotics in Health and Disease*, Journal, Indian Academy of Clinical Medicine, 6:67-72 (2005).

Vinderola, Gabriel, et al., *Role of Intestinal Epithelial Cells in Immune Effects Mediated by Gram-Positive Probiotic Bacteria: Involvement of Tol-Like Receptors*, Clinical and Diagnostic Laboratory Immunology, 12:1075-1084 (2005).

Boyle, R.J., et al., *The Role of Probiotics in the Management of Allergic Disease*, Clinical and Experimental Allergy, 36:568-576 (2006).

Laudanno, O.M., et al., *Anti-Inflammatory Effect of Bioflora Administered Orally or Subcutaneously with Live or Dead Bacteria*, 51:2180-2183 (2006).

Kaila, Minna, et al., *Viable versus inactivated lactobacillus strain GG in acute rotavirus diarrhea*, 72:51-53 (1995).

\* cited by examiner

METHOD FOR REDUCING OR PREVENTING SYSTEMIC INFLAMMATION

CROSS-REFERENCE TO RELATED PATENTS AND PATENT APPLICATIONS

This application is a Non-Provisional application and claims the priority benefit of U.S. Provisional Patent Application Ser. No. 60/904,122, filed Feb. 28, 2007, which is incorporated by reference herein in its entirety.

BACKGROUND OF THE INVENTION (1) Field of the Invention

The present invention relates generally to a method for treating or preventing systemic inflammation.

(2) Description of the Related Art

The inflammatory response is an attempt by the body to restore and maintain homeostasis after invasion by an infectious agent, antigen challenge, or physical, chemical or traumatic damage. Localized inflammation is contained in a specific region and can exhibit varying symptoms, including redness, swelling, heat and pain.

While the inflammatory response is generally considered a healthy response to injury, the immune system can present an undesirable physiological response if it is not appropriately regulated. In this situation, the body's normally protective immune system causes damage to its own tissue by treating healthy tissue as if it is infected or abnormal. Alternatively, if there is an injury, the inflammatory response may be out of proportion with the threat causing the injury. When this occurs, the inflammatory response can cause more damage to the body than the agent itself would have produced.

The inflammatory response has been found in part to consist of an increased expression of both pro-inflammatory and anti-inflammatory cytokines. Cytokines are low molecular weight, biologically active proteins involved in the coordination of immunological and inflammatory responses and communication between specific immune cell populations. A number of cell types produce cytokines during inflammatory reactions, including neutrophils, monocytes, and lymphocytes.

Multiple mechanisms exist by which cytokines generated at inflammatory sites influence the inflammatory response. If a pro-inflammatory response is not successfully countered by anti-inflammatory cytokines, however, uncontrolled systemic inflammation can occur.

In contrast to localized inflammation, systemic inflammation is widespread throughout the body. This type of inflammation may include localized inflammation at specific sites, but may also be associated with general "flu-like" symptoms, including fever, chills, fatigue or loss of energy, headaches, loss of appetite, and muscle stiffness. Systemic inflammation can lead to protein degradation, catabolism and hypermetabolism. As a consequence, the structure and function of essential organs, such as muscle, heart, immune system and liver may be compromised and can contribute to multi-organ failure and mortality. Jeschke, et al., *Insulin Attenuates the Systemic Inflammatory Response to Thermal Trauma*, Mol. Med. 8(8): 443-450 (2002). Although enormous progress has been achieved in understanding the mechanisms of systemic inflammation, the mortality rate due to this disorder remains unacceptably high.

Often, whether the cytokine response is pro- or anti-inflammatory depends on the balance of individual microorganisms that colonize the intestinal lumen at any particular time. It is well known that the mucosal surface of the intestinal tract is colonized by an enormously large, complex, and dynamic collection of microorganisms. The composition of the intestinal microflora varies along the digestive tract as well as in different micro-habitats, such as the epithelial mucus layer, the deep mucus layer of the crypts, and the surface of mucosal epithelial cells. The specific colonization depends on external and internal factors, including luminally available molecules, mucus quality, and host-microbial and microbial-microbial interactions. Murch, S. H., *Toll of Allergy Reduced by Probiotics*, Lancet, 357:1057-1059 (2001).

These microorganisms, which make up the gut microflora, are actively involved with the immune response. They interact with the epithelium in conditions of mutual beneficial relationships for both partners (symbiosis) or in conditions of benefit for one partner, without being detrimental to the other (commensalisms). Hooper, et al., *How Host-Microbial Interactions Shape the Nutrient Environment of the Mammalian Intestine*, Annu. Rev. Nutr. 22:283-307 (2002) In fact, considerable evidence is emerging which shows a strong interplay or "cross-talk" between the intestinal microflora and the diverse population of cells in the intestinal mucosa. Bourlioux, et al., *The Intestine and its Microflora are Partners for the Protection of the Host: Report on the Dan one Symposium "The Intelligent Intestine"* held in Paris, Jun. 14, 2002, Am. J. Clin. Nutr. 78:675 (2003); Hooper, L. V. & Gordon, J. I., *Commensal Host-Bacterial Relationships in the Gut*, Sci. 292:1115 (2001); Haller, et al., *Non-Pathogenic Bacteria Elicit a Differential Cytokine Response by Intestinal Epithelial Celt/Leucocyte Co-Cultures*, GUT 47:79 (2000); Walker, W. A., *Role of Nutrients and Bacterial Colonization in the Development of Intestinal Host Defense*, J. Pediatr. Gastroenterol. Nutr. 30:S2 (2000). Additionally, the gut microflora has been shown to elicit specific immune responses at both a local and systemic level in adults. Isolauri, E., et al., *Probiotics: Effects on Immunity*, Am. J. Clin. Nutr. 73:444S-50S (2001).

The gut microflora in infants is known to be far less developed than that of an adult. While the microflora of the adult human consists of more than $10^{13}$ microorganisms and nearly 500 species, some being harmful and some being beneficial, the microflora of an infant contains only a fraction of those microorganisms, both in absolute number but also species diversity. Infants are born with a sterile gut, but acquire intestinal flora from the birth canal, their initial environment, and what they ingest. Because the gut microflora population is very unstable in early neonatal life, it is often difficult for the infant's gut to maintain the delicate balance between harmful and beneficial bacteria, thus reducing the ability of the immune system to function normally.

It is especially difficult for formula-fed infants to maintain this balance due to the differences between the bacterial species in the gut of a formula-fed and breast-fed infant. The stool of breast-fed infants contains predominantly *Bifidobacterium*, with *Streptococcus* and *Lactobacillus* as less common contributors. In contrast, the microflora of formula-fed infants is more diverse, containing *Bifidobacterium* and *Bacteroides* as well as the more pathogenic species, *Staphylococcus, Escherichia coli*, and *Clostridia*. The varied species of *Bifidobacterium* in the stools of breast-fed and formula-fed infants differ as well. A variety of factors have been proposed as the cause for the different fecal flora of breast-fed and formula-fed infants, including the lower content and different composition of proteins in human milk, a lower phosphorus content in human milk, the large variety of oligosaccharides in human milk, and numerous humoral and cellular mediators of immunologic function in breast milk. Agostoni, et al., *Probiotic Bacteria in Dietetic Products for Infants. A Com-* mentary by the ESPGHAN Committee on Nutrition, J. Pediatr. Gastro. Nutr. 38:365-374 (April 2004).

Because the microflora of formula-fed infants is so unstable and the gut microflora largely participate in stimulation of gut immunity, formula-fed infants are more likely to develop inflammatory illnesses. Many of the major illnesses that affect infants, including chronic lung disease, periventricular leukomalacia, neonatal meningitis, neonatal hepatitis, sepsis, and necrotizing enterocolitis are inflammatory in nature. Depending on the particular disease, the accompanying inflammation can occur in a specific organ, such as the lung, brain, liver or intestine, or the inflammation can truly be systemic in nature.

For example, chronic lung disease causes the tissues inside the lungs to become inflamed while neonatal meningitis involves inflammation of the linings of the brain and spinal cord. Periventricular leukomalacia is caused by inflammatory damage to the periventricular area in the developing brain. Necrotizing enterocolitis causes inflammation in the intestine that may result in destruction of part or all of the intestine and neonatal hepatitis involves an inflammation of the liver that occurs in early infancy. Sepsis, also known as systemic inflammatory response syndrome, is a severe illness caused by an overwhelming infection of the bloodstream by toxin-producing bacteria. In this disease, pathogens in the bloodstream elicit an inflammatory response throughout the entire body.

Premature and critically ill infants also represent a serious challenge in terms of developing gut immunity and preventing systemic inflammation. Preterm or critically ill infants are often placed immediately into sterile incubators, where they remain unexposed to the bacterial populations to which a healthy, term infant would normally be exposed. This may delay or impair the natural colonization process. These infants are also often treated with broad-spectrum antibiotics, which kill commensal bacteria that attempt to colonize the infant's intestinal tract. Additionally, these infants are often nourished by means of an infant formula, rather than mother's milk. Each of these factors may cause the infant's gut microflora to develop improperly, thus causing or precipitating life-threatening systemic inflammation.

In recent years, the supplementation of probiotic bacteria into the diet of formula-fed infants has been suggested in order to encourage gut colonization with beneficial microorganisms. Probiotic bacteria are living microorganisms that exert beneficial effects on the health of the host. Fuller, R. *Probiotics in Man and Animals*, J. Appl. Bacteriol. 66: 365-78 (1989).

While viable probiotic bacteria may be effective in normalizing the gut microflora, there have been very few published studies assessing their safety in premature and immunosuppressed infants. These special populations have an immature gut defense barrier that increases the risk for translocation of luminal bacteria, causing a potentially heightened risk for infections. In many cases, viable probiotics are not recommended for immunosuppressed patients, post cardiac surgery patients, patients with pancreatic dysfunction, or patients with blood in the stool. At least one death has been reported due to probiotic supplementation in an immunosuppressed individual. MacGregor G., et al. *Yoghurt biotherapy: contraindicated in immunosuppressed patients?* Postgrad Med J. 78: 366-367 (2002).

Thus, for immunosuppressed patients or premature infants, it would be useful to provide a non-viable supplement that may treat or prevent systemic inflammation. A non-viable alternative to live probiotics may have additional benefits such as a longer shelf-life. Live probiotics are sensitive to heat, moisture, and light, and ideally should be refrigerated to maintain viability. Even with these precautions, the shelf-life of a typical probiotic is relatively short. A non-viable alternative to live probiotics would circumvent the necessity of refrigeration and would provide a product having a longer shelf-life. The product could then be distributed to regions of the world without readily available refrigeration. A non-viable alternative to probiotics would additionally provide less risk of interaction with other food components, such as fermentation and changes in the taste, texture, and freshness of the product. Accordingly, it would be beneficial to provide a method for reducing or preventing systemic inflammation in formula-fed infants comprising the administration of inactivated probiotics.

SUMMARY OF THE INVENTION

Briefly, therefore, the present invention is directed to a novel method for treating, preventing or reducing systemic inflammation in a subject, the method comprising administering to the subject a therapeutically effective amount of inactivated LGG.

In other embodiments, the invention is directed to a process for manufacturing a medicament for treating, preventing or reducing systemic inflammation in a subject, characterized in that at least between about $1 \times 10^4$ and $1 \times 10^{10}$ cell equivalents per kg body weight per day of inactivated *Lactobacillus rhamnosus* GG (LGG) is used as a pharmacological active substance.

In other embodiments, the invention is directed to a novel method for treating, preventing or reducing respiratory inflammation in a subject, the method comprising administering to the subject a therapeutically effective amount of inactivated LGG.

In other embodiments, the invention is directed to a method for reducing or preventing the systemic release of one or more pro-inflammatory cytokines or chemokines in a subject, the method comprising administering to the subject a therapeutically effective amount of inactivated LGG.

In another embodiment, the present invention comprises a method for preventing the ubiquitination of IkB expression in a subject, the method comprising administering to the subject a therapeutically effective amount of inactivated LGG. Further, the present invention may comprise a method for decreasing NFkB translocation in a subject, the method comprising administering to the subject a therapeutically effective amount of inactivated LGG.

In a particular embodiment, the invention is directed to a method for treating, preventing or reducing systemic or respiratory inflammation in a subject, the method comprising administering to the subject a therapeutically effective amount of inactivated LGG in combination with at least one LCPUFA and/or at least one viable probiotic. In particular embodiments, the LCPUFA may be docosahexaenoic acid (DHA) or arachidonic acid (ARA).

Among the several advantages found to be achieved by the present invention, it reduces or prevents systemic inflammation. The invention may reduce inflammation in the liver, plasma, lungs, and intestine. Additionally, the invention reduces or prevents the release of various pro-inflammatory cytokines and chemokines, including interleukin-1β (IL-1β), IL-8, CINC-1, and growth-related oncogene (GRO/KC) levels. As the present invention may be used to improve the inflammatory condition, it may also prevent the onset of deleterious infections or illnesses.

BRIEF DESCRIPTION OF THE DRAWINGS

For a more complete understanding of the present invention, reference is now made to the following descriptions taken in conjunction with the accompanying drawings.

DETAILED DESCRIPTION OF THE PREFERRED EMBODIMENTS

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

The following abbreviations are used herein: LGG, *Lactobacillus rhamnosus* GG; LCPUFA, long-chain polyunsaturated fatty acid; LPS, lipopolysaccharide; IL, interleukin; CINC-1, cytokine induced neutrophil chemoattractant-1; GRO/KC, growth-related oncogene; ELISA, enzyme-linked immunosorbent assay; RT-PCR, reverse transcription-polymerase chain reaction; ANOVA, analysis of variance; SD, standard deviation; RMS, rat milk substitute; TLRs, Toll-like receptors; Nuclear Factor kappa B, NF-κB; EPA, eicosapentaenoic acid; DHA, docosahexaenoic acid; ARA, arachidonic acid.

The terms "inactivated probiotic" or "inactivated LGG" mean that the metabolic activity or reproductive ability of the probiotic or LGG organism has been reduced or destroyed. The "inactivated probiotic" or "inactivated LGG" do, however, still retain, at the cellular level, at least a portion their biological glycol-protein and DNA/RNA structure. As used herein, the term "inactivated" is synonymous with "non-viable".

The term "probiotic" means a live, active or viable microorganism that exerts beneficial effects on the health of the host.

The term "prebiotic" means a non-digestible food ingredient that stimulates the growth and/or activity of probiotics.

As used herein, the term "treating" means ameliorating, improving or remedying a disease, disorder, or symptom of a disease or condition.

The term "reducing" means to diminish in extent, amount, or degree.

The term "preventing" means to stop or hinder a disease, disorder, or symptom of a disease or condition through some action.

The term "systemic", as used herein, means relating to or affecting the entire body.

The terms "therapeutically effective amount" refer to an amount that results in an improvement or remediation of the disease, disorder, or symptoms of the disease or condition.

The term "preterm" means an infant born before the end of the 37th week of gestation.

The term "infant" means a human that is less than about 1 year old.

The term "child" means a human between the ages of about 1 and 12 years old. In certain embodiments, a child is between the ages of about 1 and 6 years old. In other embodiments, a child is between the ages of about 7 and 12 years old.

As used herein, the term "infant formula" means a composition that satisfies the nutrient requirements of an infant by being a substitute for human milk.

In accordance with the present invention, a novel method for treating or preventing systemic inflammation has been discovered. The method comprises administering a therapeutically effective amount of inactivated LGG to a subject. In some embodiments, the subject is an infant.

Previous attempts to effectively administer inactivated probiotics have met substantial obstacles. For example, Kirjavainen, P., et al., reported that in a comparison of live and heat-inactivated LGG, nearly 40% of the children supplemented with inactivated LGG experienced severe diarrhea. *Probiotic Bacteria in the Management of Atopic Disease: Underscoring the Importance of Viability*, J. Ped. Gastro. 36: 223-227 (2003). No adverse reactions were reported in the placebo or the viable LGG group. Id. at 225. Because diarrhea is largely associated with inflammation, the Kirjavainen study indicates that inactivated LGG may actually cause gastrointestinal inflammation. In fact, the study notes, "the heat-inactivation process may cause denaturation of surface peptides and expression of heat-shock protein, thus modifying the immunostimulatory properties of LGG in such a way that the heat-inactivated form would induce inflammatory responses and consequently increase gut permeability." Id. at 226. In contrast, the present inventors have developed a novel method for treating or preventing systemic inflammation through the administration of inactivated LGG.

LGG is a probiotic strain isolated from healthy human intestinal flora. It was disclosed in U.S. Pat. No. 5,032,399 to Gorbach, et al., which is herein incorporated in its entirety, by reference thereto. LGG is resistant to most antibiotics, stable in the presence of acid and bile, and attaches avidly to mucosal cells of the human intestinal tract. It survives for 1-3 days in most individuals and up to 7 days in 30% of subjects.

In addition to its colonization ability, LGG also beneficially affects mucosal immune responses. LGG is deposited with the depository authority American Type Culture Collection under accession number ATCC 53103.

In the present invention, LGG that has been inactivated is utilized. Inactivation may occur through any method currently known in the art or yet to be developed. The inactivation may be accomplished, for example, via heat treatment, lyophilization, ultraviolet light, gamma radiation, pressure, chemical disruption, or mechanical disruption. For example, the LGG may be inactivated with heat treatment via storage between 80° C. and 100° C. for 10 minutes. The LGG may also be inactivated with ultraviolet light via irradiation for 5 minutes at a distance of 5 cm from a 30 Watt UVC lamp. Alternatively, the inactivated LGG may be inactivated with gamma radiation via irradiation with 2 kg-Gray (kGy) using a Cobalt-60 source at a distance of 20 cm.

In the method of the invention, a therapeutically effective amount of inactivated LGG is an amount sufficient to reduce or prevent systemic inflammation in a subject. This amount may correspond to between about $1\times10^4$ and $1\times10^{12}$ cell equivalents per kg body weight per day. In another embodiment, the present invention comprises the administration of between about $1\times10^6$ and $1\times10^9$ cell equivalents per kg body weight per day. In yet another embodiment, the present invention comprises the administration of about $1\times10^8$ cell equivalents per kg body weight per day.

In some embodiments of the present invention, the subject is in need of the treatment, reduction, or prevention of systemic inflammation. The subject may be at risk for systemic inflammation due to genetic predisposition, diet, lifestyle, diseases, disorders, and the like. For example, a preterm or immunosuppressed infant may be at risk for systemic inflammation and may, therefore, be in need of such treatment, reduction, or prevention.

In certain embodiments, the inactivated LGG may be administered to an infant or child to prevent, treat, or reduce systemic inflammation. In an embodiment, the infant may be less than one year of age. In another embodiment, the child may be between the ages of one and six years old. In yet another embodiment, the child may be between the ages of seven and twelve years old.

The form of administration of inactivated LGG in the method of the invention is not critical, as long as a therapeutically effective amount is administered. In some embodiments, inactivated LGG is administered to a subject via tablets, pills, encapsulations, caplets, gelcaps, capsules, oil drops, or sachets. In this embodiment of the method, an inactivated LGG supplement may be ingested in combination with other nutrient supplements, such as vitamins, or in combination with a LCPUFA supplement, such as DHA or ARA.

In another embodiment, the inactivated LGG is encapsulated in a sugar, fat, or polysaccharide. In yet another embodiment, inactivated LGG is added to a food or drink product and consumed. The food or drink product may be a children's nutritional product such as a follow-on formula, growing up milk, beverage, milk, yogurt, fruit juice, fruit-based drink, chewable tablet, cookie, cracker, or a milk powder or the product may be an infant's nutritional product, such as an infant formula.

In an embodiment, the infant formula for use in the present invention is nutritionally complete and contains suitable types and amounts of lipid, carbohydrate protein, vitamins and minerals. The amount of lipid or fat typically may vary from about 3 to about 7 g/100 kcal. The amount of protein typically may vary from about 1 to about 5 g/100 kcal. The amount of carbohydrate typically may vary from about 8 to about 12 g/100 kcal. Protein sources may be any used in the art, e.g., nonfat milk, whey protein, casein, soy protein, hydrolyzed protein, amino acids, and the like. Carbohydrate sources may be any used in the art, e.g., lactose, glucose, corn syrup solids, maltodextrins, sucrose, starch, rice syrup solids, and the like. Lipid sources may be any used in the art, e.g., vegetable oils such as palm oil, soybean oil, palmolein, coconut oil, medium chain triglyceride oil, high oleic sunflower oil, high oleic safflower oil, and the like.

Conveniently, commercially available infant formula may be used. For example, Enfamil®, Enfamil® Premature Formula, Enfamil® with Iron, Lactofree®, Nutramigen®, Pregestimil®, and ProSobee® (available from Mead Johnson & Company, Evansville, Id., U.S.A.) may be supplemented with suitable levels of inactivated LGG and used in practice of the method of the invention.

In one embodiment of the invention, inactivated LGG may be combined with one or more viable and/or inactivated probiotics to treat or prevent systemic inflammation in formula-fed infants. Any live or inactivated probiotic known in the art may be acceptable in this embodiment provided it achieves the intended result. In a particular embodiment, the viable and/or inactivated probiotic is chosen from the group consisting of *Lactobacillus* and *Bifidobacterium*.

If a live probiotic is administered in combination with the inactivated probiotic, the amount of live probiotic may correspond to between about $1\times10^4$ and $1\times10^{12}$ colony forming units (cfu) per kg body weight per day. In another embodiment, the live probiotics may comprise between about $1\times10^6$ and $1\times10^9$ cfu per kg body weight per day. In yet another embodiment, the live probiotics may comprise about $1\times10^8$ cfu per kg body weight per day.

In another embodiment of the invention, inactivated LGG may be combined with one or more prebiotics to treat or prevent systemic inflammation in formula-fed infants. Any prebiotic known in the art will be acceptable in this embodiment provided it achieves the desired result. Prebiotics of the present invention may include lactulose, galacto-oligosaccharide, fructo-oligosaccharide, isomalto-oligosaccharide, soybean oligosaccharides, lactosucrose, xylo-oligosacchairde, and gentio-oligosaccharides.

In yet another embodiment of the present invention, the infant formula may contain other active agents such as long chain polyunsaturated fatty acids (LCPUFA). Suitable LCPUFAs include, but are not limited to, α-linoleic acid, γ-linoleic acid, linoleic acid, linolenic acid, eicosapentanoic acid (EPA), ARA and DHA. In an embodiment, inactivated LGG is administered in combination with DHA. In another embodiment, inactivated LGG is administered in combination with ARA. In yet another embodiment, inactivated LGG is administered in combination with both DHA and ARA. Commercially available infant formula that contains DHA, ARA, or a combination thereof may be supplemented with inactivated LGG and used in the present invention. For example, Enfamil® LIPIL®, which contains effective levels of DHA and ARA, is commercially available and may be supplemented with inactivated LGG and utilized in the present invention.

In one embodiment, both DHA and ARA are used in combination with inactivated LGG to treat systemic inflammation in infants. In this embodiment, the weight ratio of ARA:DHA is typically from about 1:3 to about 9:1. In one embodiment of the present invention, this ratio is from about 1:2 to about 4:1. In yet another embodiment, the ratio is from about 2:3 to about 2:1. In one particular embodiment the ratio is about 2:1. In another particular embodiment of the invention, the ratio is about 1:1.5. In other embodiments, the ratio is about 1:1.3. In still other embodiments, the ratio is about 1:1.9. In a particular embodiment, the ratio is about 1.5:1. In a further embodiment, the ratio is about 1.47:1.

In certain embodiments of the invention, the level of DHA is between about 0.0% and 1.00% of fatty acids, by weight.

The level of DHA may be about 0.32% by weight. In some embodiments, the level of DHA may be about 0.33% by weight. In another embodiment, the level of DHA may be about 0.64% by weight. In another embodiment, the level of DHA may be about 0.67% by weight. In yet another embodiment, the level of DHA may be about 0.96% by weight. In a further embodiment, the level of DHA may be about 1.00% by weight.

In embodiments of the invention, the level of ARA is between 0.0% and 0.67% of fatty acids, by weight. In another embodiment, the level of ARA may be about 0.67% by weight. In another embodiment, the level of ARA may be about 0.5% by weight. In yet another embodiment, the level of DHA may be between about 0.47% and 0.48% by weight.

The effective amount of DHA in an embodiment of the present invention is typically from about 3 mg per kg of body weight per day to about 150 mg per kg of body weight per day. In one embodiment of the invention, the amount is from about 6 mg per kg of body weight per day to about 100 mg per kg of body weight per day. In another embodiment the amount is from about 10 mg per kg of body weight per day to about 60 mg per kg of body weight per day. In yet another embodiment the amount is from about 15 mg per kg of body weight per day to about 30 mg per kg of body weight per day.

The effective amount of ARA in an embodiment of the present invention is typically from about 5 mg per kg of body weight per day to about 150 mg per kg of body weight per day. In one embodiment of this invention, the amount varies from about 10 mg per kg of body weight per day to about 120 mg per kg of body weight per day. In another embodiment, the amount varies from about 15 mg per kg of body weight per day to about 90 mg per kg of body weight per day. In yet another embodiment, the amount varies from about 20 mg per kg of body weight per day to about 60 mg per kg of body weight per day.

The amount of DHA in infant formulas for use with the present invention typically varies from about 5 mg/100 kcal to about 80 mg/100 kcal. In one embodiment of the present invention, DHA varies from about 10 mg/100 kcal to about 50 mg/100 kcal; and in another embodiment, from about 15 mg/100 kcal to about 20 mg/100 kcal. In a particular embodiment of the present invention, the amount of DHA is about 17 mg/100 kcal.

The amount of ARA in infant formulas for use with the present invention typically varies from about 10 mg/100 kcal to about 100 mg/100 kcal. In one embodiment of the present invention, the amount of ARA varies from about 15 mg/100 kcal to about 70 mg/100 kcal. In another embodiment, the amount of ARA varies from about 20 mg/100 kcal to about 40 mg/100 kcal. In a particular embodiment of the present invention, the amount of ARA is about 34 mg/100 kcal.

The infant formula supplemented with oils containing DHA and ARA for use with the present invention may be made using standard techniques known in the art. For example, they may be added to the formula by replacing an equivalent amount of an oil, such as high oleic sunflower oil, normally present in the formula. As another example, the oils containing DHA and ARA may be added to the formula by replacing an equivalent amount of the rest of the overall fat blend normally present in the formula without DHA and ARA.

The source of DHA and ARA may be any source known in the art such as marine oil, fish oil, single cell oil, egg yolk lipid, brain lipid, and the like. The DHA and ARA can be in natural form, provided that the remainder of the LCPUFA source does not result in any substantial deleterious effect on the infant. Alternatively, the DHA and ARA can be used in refined form.

In an embodiment of the present invention, sources of DHA and ARA are single cell oils as taught in U.S. Pat. Nos. 5,374,567; 5,550,156; and 5,397,591, the disclosures of which are incorporated herein in their entirety by reference. However, the present invention is not limited to only such oils.

In one embodiment, the LCPUFA source contains EPA. In another embodiment, the LCPUFA source is substantially free of EPA. For example, in one embodiment of the present invention the infant formula contains less than about 16 mg EPA/100 kcal; in another embodiment less than about 10 mg EPA/100 kcal; and in yet another embodiment less than about 5 mg EPA/100 kcal. One particular embodiment contains substantially no EPA. Another embodiment is free of EPA in that even trace amounts of EPA are absent from the formula.

It is believed that the provision of the combination of inactivated LGG with DHA and/or ARA provides complimentary or synergistic effects with regards to the anti-inflammatory properties of formulations containing these agents. While not wishing to be tied to this or any other theory, it is believed that inactivated LGG imparts anti-inflammatory effects, in part, by preventing the ubiquitination of inhibitory-kB (IkB). In a normal cell, IkB binds nuclear factor-kB (NFkB) within the cytoplasm. When ubiquitination of IkB occurs, NFkB is released, enters the nucleus of the cell, and activates genes that are responsible for the inflammatory response. It is this specific interaction and resulting alteration in gene expression that is thought to be involved in the modulation of inflammation. It is believed that inactivated LGG prevents the ubiquitination of IkB, thereby preventing the release of NFkB and reducing or preventing inflammation.

In contrast, ω-3 fatty acids such as DHA are thought to impart anti-inflammatory action through altering the production of pro-inflammatory, fatty acid-derived, mediators broadly known as eicosanoids. ω-6 fatty acids, such as ARA, which are located in the phospholipid pool of cell membranes, are released during the inflammatory response and liberate a pool of free ARA. This pool of ARA is then acted upon by two classes of enzymes, known as lipoxygenases and cyclooxygenases, which produce a specific spectrum of eicosanoids including the 2-series prostanoids, such as prostaglandins, thromboxanes, and leukotrienes.

These eicosanoids are known to have a plethora of pro-inflammatory actions in many cell types and organs. It is known that diets rich in ω-3 fatty acids, such as EPA and DHA, are competitors for ω-6 fatty acids in several steps of this process and, therefore, moderate the pro-inflammatory effects of ARA. For example, ω-3 fatty acids modulate the elongation of the ω-6 fatty acids into ARA, the incorporation of ARA into the cell membrane phospholipid pool, and the production of pro-inflammatory eicosanoids from ARA. The combination of DHA and ARA, therefore, provides distinct, but complimentary, actions to moderate the inflammatory response in multiple tissues.

In addition, in some embodiments of the invention, live and inactivated LOG are administered in combination with one another. The combination of live and inactivated LGG is believed to provide complimentary or synergistic effects with regards to the anti-inflammatory properties of formulations containing these agents. While not wishing to be tied to this or any other theory, live probiotics such as LGG are thought to impart anti-inflammatory effects in part through interaction with specific receptors, known as Toll-like receptors (TLRs) on the surface of specific immune cells. Direct or indirect interaction between live LGG and these receptors initiates an intracellular signal transduction cascade that results in the alteration of gene expression in these target cells. It is this specific interaction and resulting alteration in gene expression and other cellular effects that is thought to be involved in the modulation of inflammation. Thus, because live and inactivated LGG are believed to operate through different mechanisms, it is believed that the combination of these components provides complimentary or synergistic anti-inflammatory effects.

In addition, in some embodiments of the invention, live LGG, inactivated LGG, and at least one LCPUFA are administered in combination. Because live LGG, inactivated LGG, and LCPUFAs are each believed to operate through different mechanisms, it is believed that the combination of these components provides complimentary or synergistic effects with regards to the anti-inflammatory properties of formulations containing these agents.

In an embodiment of the present invention, the subject is a formula-fed infant. In one embodiment, the infant is formula-fed from birth. In another embodiment, the infant is breast-fed from birth until an age which is less than one year, and is formula-fed thereafter, at which time inactivated LGG supplementation begins.

In a particular embodiment of the present invention, the method comprises treating or preventing systemic inflammation in a formula-fed preterm infant. In this method, inactivated LGG may be administered to the preterm infant in the form of an infant formula or any other suitable form. Additionally, if desired, inactivated LGG may be administered to the preterm in combination with DHA, ARA, and/or one or more live probiotics to create a potentially synergistic anti-inflammatory effect.

In a method of the present invention, inactivated LGG reduces or prevents the systemic release of one or more pro-inflammatory cytokines or chemokines. As used herein, "pro-inflammatory" cytokines or chemokines include those known in the art to be involved in the up-regulation of inflammatory reactions. Examples include, but are not limited to, TNF-α, IL-1β, IL-6, IL-8, IL-18, and GRO/KC.

Chemokines are a group of cytokines that enable the migration of leukocytes from the blood to the tissues at the site of inflammation. When produced in excess amounts, chemokines can lead to damage of healthy tissue. Growth-related oncogene (GRO/KC) is a chemokine which recruits immune cells to the site of inflammation. It is the human counterpart to rat cytokine-induced neutrophil chemoattractant (CINC-1), and is functionally related to the interleukin-8 family.

In a further embodiment of the invention, inactivated LGG has been shown to inhibit the translocation of nuclear factor-kB (NFkB). NFkB is a primary transcription factor found in all cell types which is thought to play an important role in onset of inflammation. In most cells, NF-kB is present as a latent, inactive, inhibitory kB (IkB)-bound complex in the cytoplasm. When a cell receives any of a multitude of extracellular signals, such as from cytokines, bacterial antigens, or free radicals, NF-kB rapidly enters the nucleus and activates genes that are responsible for the inflammatory response. It has been shown that inhibition of NFκB at the onset of inflammation results in a decreased inflammatory response. Lawrence, et al, *Possible New Role for NFkB in the Resolution of Inflammation*, Nature Med. 7: 1291 (2001). Thus, the inhibition of NFkB via inactivated LGG supplementation in the present invention aids in the reduction or prevention of systemic inflammation.

As will be seen in the examples, inactivated LGG has been shown to reduce systemic inflammation in formula-fed infants. CINC-1 and various cytokine levels in the formula-fed rat infants were reduced to levels similar to that of mother's milk fed rat infants when supplemented with LGG.

As will be seen in the examples, inactivated LGG has also been shown to significantly reduce IL-8 production, decrease NF-κB translocation, and increase IkB production in the intestinal epithelium. The inventors have surprisingly discovered that inactivated LGG additionally prevents the ubiquitination of IkB, while live LGG does not.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

EXAMPLE 1

This example illustrates the effect of inactivated LGG on systemic inflammation in formula-fed neonatal rat pups.

Materials & Methods

In two separate experiments, Sprague-Dawley (Taconic, Germantown, N.Y.) infant rats were randomly assigned to four gastrostomy feeding groups with five rats per group: a control group (no LPS or LGG), an LPS group, an LPS plus live LGG group, and an LPS plus inactivated LGG group. Mother-reared rats of the same age were used as reference controls. Gastrostomy feeding, using the rat infant "pup-in-the-cup" model, began on day 7 of life of the rat pups. The gastrostomy feeding tubes were constructed from 24-cm sections of polyethylene tubing that were inserted into the stomach of the pups. The gastrostomy placement was done under isoflurane anesthesia. Timer-controlled syringe pumps were connected to the feeding tubes and were set to feed the rats for the first 20 minutes of every hour at a weight-dependent flow rate.

During a 2-day acclimation period, the gastrostomy-fed rat pups were fed with rat milk substitute (RMS). After the acclimation period, one of the RMS fed groups was given a supplement of $1 \times 10^8$ cell equivalents per kg body weight per day of inactivated LGG. The LGG was inactivated via lethal heat treatment. A second group was given a supplement of $1 \times 10^8$ cfu/L per kg body weight per day of live LGG. The third group was fed RMS without LGG supplementation of any type. These feedings continued for 6 days. All of the gastrostomy-fed groups received the same quantity of fat and carbohydrates, and the protein component was similar to the quantity required for normal growth. Mother-reared rats of the same age were used as reference controls.

Lipopolysaccharide (LPS) from *Escherichia coli* 0127: B8 (LPS; Sigma, St. Louis, Mo.) was dissolved in water by vortexing at a concentration of 2 mg/ml. The gastrostomy-fed rats were given between 0.25 and 0.5 mg/kg/day of LPS via the gastrostomy tube starting 2 days after the initiation of artificial feeding. The pups were given LPS supplementation for 6 days. This dose was determined in pilot studies to result in occasional shivering, piloerection, and poor weight gain but was not associated with a significant increase in mortality over a 6-day period.

At the end of the 6-day treatment period, the rat pups were euthanized with an overdose of pentobarbital sodium. The small intestine was removed and separated into three parts: the ileum, jejunum, and duodenum, stored at −80° C. for enzyme assays and ELISA, or fixed in 10% neutral buffered formalin for intestinal morphology. Lung, liver and plasma were stored at −80° C. for enzyme assays and ELISA.

Sigmastat statistical software (SPSS, Chicago, Ill.) was used to analyze body weight, ELISA for CINC-1, and cytokine/chemokine multiplex assay results. All data were reported as means±standard deviation (SD). A one-way analysis of variance between groups (ANOVA) was used to determine whether a significant difference was present among all treatment groups. The Holm-Sidak method was performed for pairwise comparisons when the ANOVA was significant at $p < 0.05$.

Results & Discussion
Growth

This example illustrates the effect of LGG on the growth of pups after gastrostomy feeding. The rat pups were weighed daily after the gastrostomy feeding and compared to mother-fed reference animals. Mother-fed animals grew more rapidly than the LPS-treated, gastrostomy-fed pups. Providing live or inactivated LGG to gastrostomy-fed, LPS treated pups did not improve weight gain.

CINC-1

Live and inactivated LGG reduced CINC-1 levels in the present invention. CINC-1 levels were determined by TiterZyme Enzyme Immunometric Assay kits for rat growth-related oncogene/CINC-1 (Assay Designs, Ann Arbor, Mich.). Tissue samples were isolated from cellular extracts of whole tissues in the liver, intestine, plasma, and lung. Absorbance was determined at 450 nm, and concentration was calculated using the equation derived from a linear standard curve.

Figure 1:
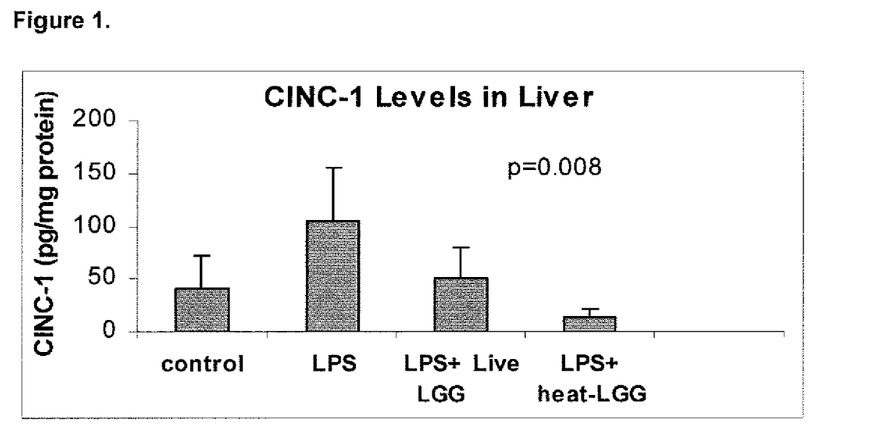
FIG. 1 illustrates the effect of live and inactivated LGG on cytokine induced neutrophil chemoattractant-1 (CINC-1) peptide production in the liver using enzyme-linked immunosorbent assay (ELISA). Inactivated LGG is labeled as "heat-LGG".
Figure 2:
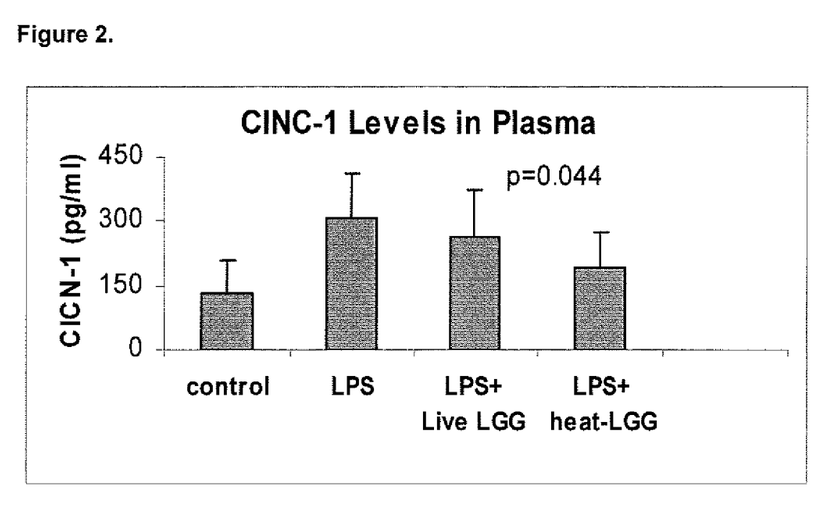
FIG. 2 illustrates the effect of live and inactivated LGG on cytokine induced neutrophil chemoattractant-1 (CINC-1) peptide production in plasma using enzyme-linked immunosorbent assay (ELISA). Inactivated LGG is labeled as "heat-LGG".
Figure 3:
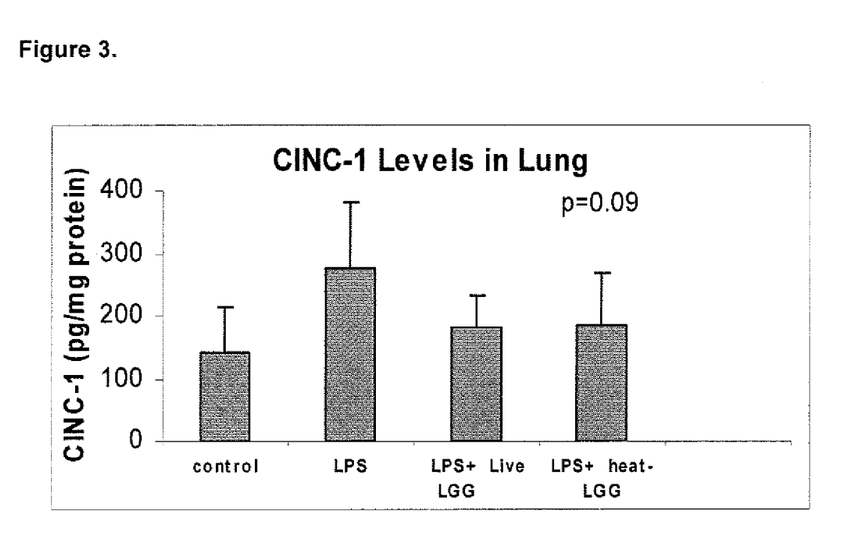
FIG. 3 illustrates the effect of live and inactivated LGG on cytokine induced neutrophil chemoattractant-1 (CINC-1) peptide production in the lung using enzyme-linked immunosorbent assay (ELISA). Inactivated LGG is labeled as "heat-LGG".

As shown in FIGS. 1 through 3, ELISA results showed that LPS increased CINC-1 levels in the liver, lungs, and plasma. Both live and inactivated LGG decreased LPS-induced CINC-1 production in the liver (FIG. 1) and plasma (FIG. 2) ($p < 0.05$), and also showed a trend ($p = 0.09$) in the lung (FIG. 3).

FIG. 1 illustrates that live LGG supplementation reduced CINC-1 levels in the liver by approximately 50% when compared to the LPS group. Inactivated LGG, however, reduced CINC-1 levels in the liver by about 75% when compared to the LPS group. Thus, inactivated LGG had a significantly greater reducing effect on liver CINC-1 levels than live LGG did, indicating a stronger anti-inflammatory effect. Similarly, FIG. 2 illustrates that CINC-1 levels in the plasma were lower in the inactivated LGG group than they were in the live LGG group. In the lung, both live and inactivated LGG reduced CINC-1 levels to a similar degree (FIG. 3).

GRO/KC

Figure 4:
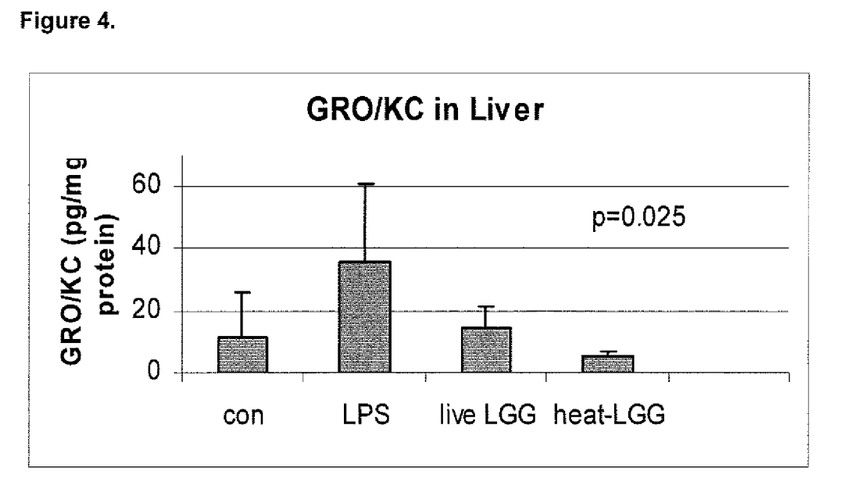
FIG. 4 illustrates the effect of live and inactivated LGG on growth-related oncogene (GRO/KC) production in the liver using a cytokine multiplex assay. Inactivated LGG is labeled as "heat-LGG".
Figure 5:
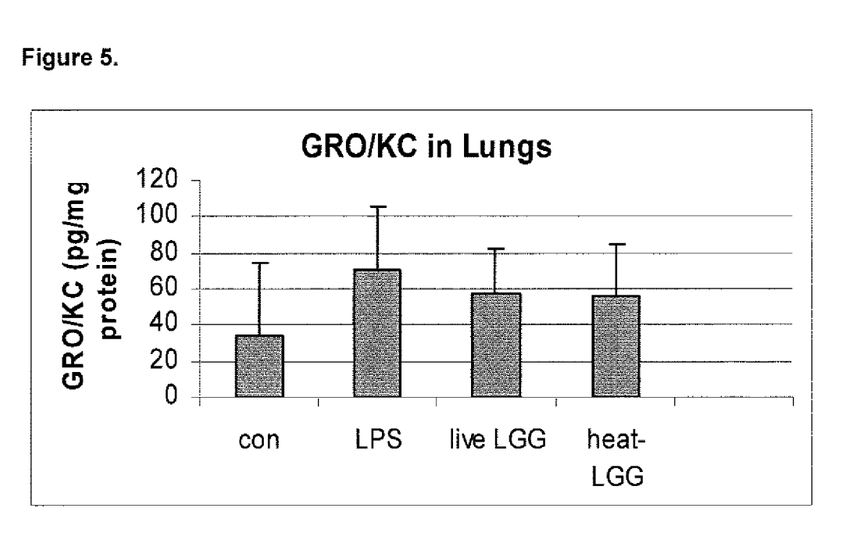
FIG. 5 illustrates the effect of live and inactivated LGG on growth-related oncogene (GRO/KC) production in the lung using a cytokine multiplex assay. Inactivated LGG is labeled as "heat-LGG".

As shown in FIGS. 4 and 5, the cytokine multiplex assay showed similar reductions in GRO/KC levels in the liver and lungs. The inactivated LGG decreased GRO/KC levels to a greater extent than live LGG in the liver, indicating a stronger anti-inflammatory effect (FIG. 4). Both live and inactivated LGG reduced GRO/KC levels to a similar degree in the lungs (FIG. 5).

The reduced CINC-1 and GRO/KC levels that were observed in the lung in the present experiment indicate that the anti-inflammatory effect of inactivated LGG extends to distal organs. Thus, they anti-inflammatory effect of inactivated LGG is truly systemic in nature.

In the liver, inactivated LGG supplementation reduced CINC-1 levels to a level which was actually lower than that of mother's milk-fed rat pups. In the lung and plasma, inactivated LGG reduced CINC-1 levels to a level which was very similar to that of mother's milk-fed rat pups. These results show that inactivated LGG has the ability to reduce systemic inflammation in a formula-fed infant to a level which is similar to, and in some cases lower than, that of a breast-fed infant.

Cytokines & Chemokines

Live and inactivated LGG also reduced cytokine and chemokine levels. Multiplex bead kits were purchased from LINCO Research, Inc. (St. Charles, Mo., USA). Cytokines/chemokines were analyzed by a kit that included: granulocyte-macrophage colony-stimulating factor (GMCSF), interferon-$\lambda$ (IFN-$\lambda$), interleukin-1$\alpha$ (IL-1$\alpha$), IL-1$\beta$, IL-2, IL-4, IL-5, IL-6, IL-8, IL-10, IL-12p70, IL-18, Monocyte Chemoattractant protein-1 (MCP-1), GRO/KC (rat CINC-1), and TNF-$\alpha$. The multiplex assay was performed according to the manufacturers specifications. Standard curves for each cytokine/chemokine were generated by using the reference concentrations supplied by the manufacturers. Raw data (mean fluorescent intensity) were analyzed by MasterPlex Quantitation Software (MiraiBio, Inc., Alameda, Calif., USA) to obtain concentration values.

Figure 6:
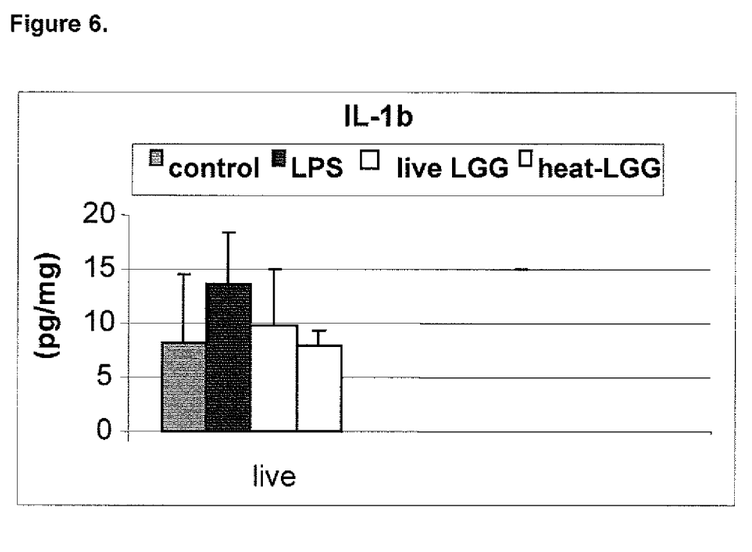
FIG. 6 illustrates the effect of live and inactivated LGG on IL-1β levels in the liver using a cytokine multiplex assay. Inactivated LGG is labeled as "heat-LGG".

As shown in FIG. 6, IL-1$\beta$ levels in the liver were significantly higher in gastrostomy-fed, LPS-treated pups than in control pups. Both live and inactivated LGG significantly blunted the LPS induced elevation of IL-1$\beta$. In fact, inactivated LGG reduced IL-1$\beta$ levels to a greater extent than live LGG supplementation did. Inactivated LGG lowered IL-1$\beta$ expression to a level which was similar to that of the control pups. Thus, this portion of the experiment further illustrates inactivated LGG's systemic anti-inflammatory activity.

In conclusion, these results show that inactivated LGG supplementation reduces systemic inflammation. Further, the results show that inactivated LGG reduces systemic inflammation in formula-fed infants to a level which is similar to that of breast-fed infants. This is illustrated in the results described herein through comparison of the inactivated LGG-treated group and the group exclusively fed mother's milk. In several instances, administration of inactivated LGG results in an inflammatory response that is very similar to that of the mother's milk-fed group.

EXAMPLE 2

This example further illustrates the effect of inactivated LGG on inflammation in formula-fed neonatal rat pups.

Intestinal epithelial cells were pretreated with live or UV-inactivated LGG at $1 \times 10^8$ cfu/L and then stimulated by Flagellin 500 ng/mL. IL-8 production was measured by ELISA. IkB and ubiquitinated-IkB (UbQ-IkB) expression were measured by Western Blotting and immunoprecipitation. NFkB localization was evaluated by immunofluorescence staining.

During the experiment, Flagellin induced a significant increase in cellular IL-8 production ($p < 0.05$). Cells pretreated with either live LGG or UV-inactivated LGG and then stimulated by Flagellin showed a significant ($p < 0.05$) change in IL-8, NFkB nuclear translocation, IkB, and UbQ-IkB. The results are shown in Table 1. Arrows pointing upwardly indicate an increase in the parameter, while arrows pointing downwardly indicate a decrease in the parameter.

TABLE 1

Expression Changes Due to Live or Inactivated LGG Supplementation.

|  | IL-8 | NFkB Translocation | IkB | UbQ-IkB |
|---|---|---|---|---|
| Flagellin alone | ↑ | ↑ | ↓ | ↑ |
| Live LGG | ↓ | ↓ | ↑ | ↑ |
| Inactivated LGG | ↓ | ↓ | ↑ | ↓ |

As shown in Table 1, Flagellin induced a significant increase in intestinal epithelial cellular IL-8 production ($p<0.05$). IL-8 production was significantly downregulated in the presence of both live and inactivated LGG. In addition, cells stimulated by Flagellin showed NFkB nuclear translocation, which was prevented by both live and inactivated LGG. Flagellin decreased IkB production, but this effect was reversed by both live and inactivated LGG pretreatment ($p<0.05$). Flagellin and live LGG increased UbQ-IkB ($p<0.05$), while inactivated LGG decreased UbQ-IkB.

This example illustrates that both live and inactivated LGG are effective in decreasing the production of IL-8, a pro-inflammatory cytokine, and thereby have an anti-inflammatory effect. Because Flagellin and live LGG increased UbQ-IkB, but inactivated LGG decreased UbQ-IkB, inactivated LGG likely operates through a mechanism that prevents the ubiquitination of IkB, while live LGG likely does not. Thus, this example further illustrates that live and inactivated LGG likely operate through different mechanisms and may have synergistic effects when administered together.

The present invention has been shown to reduce inflammation in the liver, plasma, and lungs. As the present invention may be used to improve the inflammatory condition, it may also prevent the onset of deleterious infections or illnesses.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What is claimed is:

1. A method for reducing the systemic release of one or more pro-inflammatory cytokines in an infant experiencing intestinal inflammation, the method comprising the step of: administering to the infant a nutritional composition, wherein the nutritional composition is formulated to provide the infant between about $1\times10^4$ and about $1\times10^{10}$ cells of inactivated Lactobacillus rhamnosus GG per kg body weight per day.

2. The method of claim 1, wherein the nutritional composition is further formulated to provide between about 5 mg to about 150 mg per kg of body weight per day of arachidonic acid and between about 3 mg to about 150 mg per kg of body weight per day of docosahexaenoic acid.

3. The method of claim 1, wherein the one or more pro-inflammatory cytokines are selected from the group consisting of interleukin-1β, interleukin-8, cytokine-induced neutrophil chemoattractant 1, and growth-related oncogene.

4. The method of claim 1, wherein the infant is a preterm infant.

5. The method of claim 2, wherein the arachidonic acid is provided in an amount of between about 15 mg to about 90 mg per kg of body weight per day.

6. The method of claim 2, wherein the docosahexaenoic acid is provided in an amount of between about 15 mg to about 90 mg per kg of body weight per day.

7. The method of claim 1, wherein the inactivated Lactobacillus rhamnosus GG is provided in an amount sufficient to provide between about $1\times10^6$ and $1\times10^9$ cells of inactivated Lactobacillus rhamnosus GG per kg body weight per day.

8. The method of claim 1, wherein the nutritional composition does not comprise eicosapentaenoic acid.

9. The method of claim 1, wherein the nutritional composition further comprises a prebiotic.

10. A method for reducing the systemic release of one or more pro-inflammatory cytokines in an infant experiencing hepatic inflammation, the method comprising the step of: administering to the infant a nutritional composition, wherein the nutritional composition is formulated to provide between about $1\times10^4$ and $1\times10^{10}$ cells of inactivated Lactobacillus rhamnosus GG per kg body weight per day.

11. The method of claim 10, wherein the nutritional composition is further formulated to provide between about 5 mg to about 150 mg per kg of body weight per day of arachidonic acid and between about 3 mg to about 150 mg per kg of body weight per day of docosahexaenoic acid.

12. The method of claim 11, wherein the arachidonic acid is provided in an amount of between about 15 mg to about 90 mg per kg of body weight per day.

13. The method of claim 11, wherein the docosahexaenoic acid is provided in an amount of between about 15 mg to about 90 mg per kg of body weight per day.

14. The method of claim 10, wherein the inactivated Lactobacillus rhamnosus GG is provided in an amount sufficient to provide between about $1\times10^6$ and $1\times10^9$ cells of inactivated Lactobacillus rhamnosus GG per kg body weight per day.

15. The method of claim 10, wherein the one or more pro-inflammatory cytokines are selected from the group consisting of interleukin-1β, interleukin-8, cytokine-induced neutrophil chemoattractant 1, and growth-related oncogene.

16. The method of claim 10, wherein the infant is a preterm infant.

17. The method of claim 10, wherein the nutritional composition does not comprise eicosapentaenoic acid.

18. The method of claim 10, wherein the nutritional composition further comprises a prebiotic.

19. A method for preventing the translocation of nuclear factor-kβ (Nkβ) in an infant experiencing systemic inflammation, the method comprising the step of administering to an infant a nutritional composition formulated to provide between about $1\times10^4$ and $1\times10^{10}$ cells of inactivated Lactobacillus rhamnosus GG per kg body weight per day.

20. The method of claim 19, wherein the nutritional composition is further formulated to provide between about 5 mg to about 150 mg per kg of body weight per day of arachidonic acid and between about 3 mg to about 150 mg per kg of body weight per day of docosahexaenoic acid.

* * * * *